(12) United States Patent
Bouget et al.

(10) Patent No.: US 8,338,134 B2
(45) Date of Patent: Dec. 25, 2012

(54) **EXPRESSION OF POLYPEPTIDES FROM THE NUCLEAR GENOME OF *OSTREOCOCCUS* SP**

(75) Inventors: François-Yves Bouget, Perpignan (FR); Florence Corellou, Perpignan (FR)

(73) Assignees: Centre National de la Recherche Scientifique - CNRS, Paris (FR); Universite Pierre et Marie Curie, Paris (FR)

( * ) Notice: Subject to any disclaimer, the term of this patent is extended or adjusted under 35 U.S.C. 154(b) by 399 days.

(21) Appl. No.: 12/526,171

(22) PCT Filed: Feb. 8, 2008

(86) PCT No.: PCT/IB2008/000281
§ 371 (c)(1), (2), (4) Date: Sep. 21, 2009

(87) PCT Pub. No.: WO2008/096250
PCT Pub. Date: Aug. 14, 2008

(65) Prior Publication Data
US 2010/0174050 A1 Jul. 8, 2010

Related U.S. Application Data

(60) Provisional application No. 60/900,464, filed on Feb. 9, 2007.

(51) Int. Cl.
C12N 1/20 (2006.01)
C12N 15/00 (2006.01)
C12P 21/06 (2006.01)
(52) U.S. Cl. .................. 435/69.1; 435/252.3; 435/320.1
(58) Field of Classification Search .................. None
See application file for complete search history.

(56) References Cited

U.S. PATENT DOCUMENTS

| | | | |
|---|---|---|---|
| 6,027,900 | A | 2/2000 | Allnutt et al. |
| 6,156,517 | A | 12/2000 | Mayfield |
| 6,294,653 | B1 | 9/2001 | Mayfield |
| 2003/0066107 | A1 | 4/2003 | Xue et al. |
| 2004/0014174 | A1 | 1/2004 | Mayfield et al. |
| 2005/0282247 | A1 | 12/2005 | Wu et al. |
| 2006/0137042 | A1 | 6/2006 | Plesch et al. |

FOREIGN PATENT DOCUMENTS

| | | |
|---|---|---|
| EP | 0 659 216 | 6/1995 |
| WO | WO 02/26943 | 4/2002 |
| WO | WO 2006/040764 A2 | 4/2006 |

OTHER PUBLICATIONS

Yoram Tekoah et al., "Controlled glycosylation of therapeutic antibodies in plants", Archives of Biochemistry and Biophysics, Jun. 15, 2004, pp. 266-278, vol. 426, No. 2, New York, US.
Kevin M. Cox et al., "Glycan optimization of a human monoclonal antibody in the aquatic plant Lemna minor", Nature Biotechnology, Nature Publishing Group, Dec. 1, 2006, pp. 1591-1597, vol. 24, No. 12, New York, New York, US.
Mayfield Stephen P et al., "Expression and assembly of a fully active antibody in algae", Proceedings of the National Academy of Sciences of USA, National Assembly of Science, Jan. 21, 2003, pp. 438-442, vo. 100, No. 2, Washington, DC.
Derelle Evelyne et al., "Genome analysis of the smallest free-living eukaryote *Ostreococcus tauri* unveils many unique features", Proceedings of the National Academy of Sciences of USA, National Academy of Science, Aug. 1, 2006, pp. 11647-11652, vol. 103, No. 31, Washington, DC.
Coll J M, "Methodologies for transferring DNA into eukaryotic microalgae", Spanish Journal of Agriculture Research, Dec. 2006, pp. 316-330, vol. 4, No. 4.
Walker et al., "Algal Transgenics In The Genomic Era", J. Phycol, pp. 1077-1093, vol. 41, 2005 Phycological Society of America.
Leon-Banares R et al., "Transgenic microalgae as green cell-factories", Trends in Biotechnology, Jan. 1, 2004, pp. 45-52, vol. 22, No. 1, Elsevier Publication, Cambridge, GB.
Walker Tara et al., "Microalgae as bioreactors", Plant Cell Reports Dec. 2005, pp. 629-641, vol. 24, No. 11.
S. E. Franklin et al, "Recent developments in the production of human therapeutic proteins in eukaryotic algae" Expert Opin Biol Ther 5, 2005, 225-235.
K. Ko et al, "Plant biopharming of monoclonal antibodies", Virus Res 111, 2005, 93-100.
K. Ko et al, "Inhibition of tumor growth by plant-derived mAb" Proc Natl Acad Sci U.S.A., 102, 2005, 7026-30.
F. Domergue et al, "In vivo characterization of the first acyl-CoA $\Delta^6$-desaturase from a member of the plant kingdom, the microalga *Ostreococcus tauri*", Biochem J., 389, 2005, 483-490.
S. Robbens et al, "Genome-Wide Analysis of Core Cell Cycle Genese in the Unicellular Green Alga *Ostreococcus tauri*", Mol. Biol. Evol., 22(3), 2005, 589-597.
L. Faye et al, <<La production de protéines à usage biopharmaceutique dans les plantes >>, médecine/sciences, 17, 2001, 867-77. [In French].
Arago Laboratory: "Structure génomique et dtratégie adaptative de l'aigue vert unicellulaire Ostrococcus tauri", 2005. [In french].

*Primary Examiner* — Albert Navarro
(74) *Attorney, Agent, or Firm* — Arent Fox LLP

(57) ABSTRACT

A method of producing at least one polypeptide from the nuclear genome of *Ostreo-coccus* sp., the method including introducing at least one recombinant nucleic acid molecule into the nuclear genome of *Ostreococcus* sp., wherein the recombinant nucleic acid molecule included a first polynucleotide operatively linked to a second polynucleotide, wherein the second polynucleotide encodes at least one polypeptide and wherein the first polynucleotide comprises a promoter sequence allowing expression of the at least one polypeptide in *Ostreoccus* sp.

34 Claims, 8 Drawing Sheets

| 470470 | 284280 | 4470 | 154340 | 151910 | 190 | 170 | 1324370 | 2360 | 6160 | 880500 |
|---|---|---|---|---|---|---|---|---|---|---|
| 96380 | 9360 | 318060 | 31780 | 290 | 7170 | 9300 | 550 | 34350 | 3820 | 21280 |
| 29070 | 164480 | 25210 | 1112100 | 240 | 170 | | | | | |

Figure 3

EXPRESSION OF POLYPEPTIDES FROM THE NUCLEAR GENOME OF *OSTREOCOCCUS* SP

CROSS-REFERENCE TO RELATED APPLICATION

This application is a National Stage entry on International Application PCT/IB2008/000281, filed Feb. 8, 2008, which claims priority to U.S. Patent Application No. 60/900,464, filed Feb. 9, 2007, the disclosure of the prior applications being incorporated in their entirety by reference.

SEQUENCE LISTING

The instant application contains a Sequence Listing which has been submitted via EFS-Web and is hereby incorporated by reference in its entirety. Said ASCII copy, created on Jan. 27, 2010, is named 21305279.txt, and is 23,840 bytes in size.

TECHNICAL FIELD

The technology in this disclosure relates generally to the field of methods for expressing polypeptides from the nuclear genome of green algae, particularly in *Ostreococcus* sp.

PRIOR ART

The production of recombinant proteins and in particular of monoclonal antibodies represents an important market and is in full expansion. It is evaluated to 10 billions dollars in 2004 and it should exceed 30 billions dollars in 2010. These recombinant proteins are finding use as supplements for healthy individuals or as therapeutic agents for the treatment of pathologic disorder, particularly in cancerology and in infectious diseases.

A primary advantage of using genetic engineering techniques for producing therapeutic agents is that the methods allow for the generation of large amounts of a desired protein. Different methods using different cell types were developed until now. Even where technologies based on bacteria cells were improved, they present limitations for the production of complex proteins such as antibodies. Methods using eukaryotic cells, particularly insect cells and mammalian cells allow for the production of human complex proteins. However, the high cost of these systems constituted the principal limitation of their development.

The production of proteins in transgenic plants currently constitutes an alternative in full rise. These expression systems allow for the production of complex proteins without carrying pathogenic agents like viruses and prions. The main problem with the use of transgenic plants is the risk of contamination relating to the pollen dissemination, especially using human genes or allergens. In fact, the European legislation limits the use of transgenic plants due to such risk. In addition, if such production is cheap, the purification of proteins from the plants can be complex and expansive.

Recently a green algae, i.e. *Chlamydomonas reinhardtii*, has been used to produce a monoclonal antibody directed to the Herpes virus from its plastidial genome. This algae presents the main advantage to be unicellular and thus to facilitate the purification of recombinant proteins compared with transgenic plants. However, the biased genetic code of *Chlamydomonas reinhardtii* constitutes the major drawback of this expression system. In fact, it is necessary to genetically modify each codon of a gene comprising A or T at the third position, to obtain a correct expression of a recombinant protein coded by said gene. This required step for the production of protein involves a high production cost for this expression system in *Chlamydomonas reinhardtii*. Furthermore, expression in the plastid does not allow the glycosylation of glycolproteins, such as antibodies, which is often required for their biological activity or stability.

Thus, a need exists for methods to conveniently produce and purify proteins in large amounts with low cost.

DEPOSIT INFORMATION

An isolated strain of *Ostreococcus tauri* OTTH95 was deposited pursuant to the Budapest Treaty on the International Recognition of the Deposit of Microorganisms for the Purposes of Patent Procedure in the Culture Collection of Algae and Protozoa (CCAP), at SAMS Research Services Ltd., Oban, Argyll PA37 IQA, Scotland, United Kingdom, on Nov. 14, 2006. The deposit was accepted on Dec. 14, 2006, and designated as CCAP Number 157/1.

SUMMARY

Recombinant proteins can be expressed from *Ostreococcus* sp. green algae nuclear genome. Accordingly, we provide a method of producing at least one polypeptide in *Ostreococcus* sp., the method comprising introducing at least one recombinant nucleic acid molecule into *Ostreococcus* sp., wherein the recombinant nucleic acid molecule comprises a first polynucleotide operatively linked to a second polynucleotide, wherein the second polynucleotide encodes at least one polypeptide and wherein the first polynucleotide comprises a promoter sequence allowing expression of the at least one polypeptide in *Ostreococcus* sp.

We further provide an expression cassette for expression of at least one polypeptide in *Ostreococcus* sp., which cassette comprises a promoter sequence operatively linked to and positioned upstream of a restriction enzyme site for insertion of a nucleotide sequence coding for the at least one polypeptide, wherein the promoter sequence allows expression of the at least one polypeptide in *Ostreococcus* sp.

We still further provide a vector comprising at least one expression cassette according to the invention as described below.

We yet further provide a cell, which can be obtained by the method according to the invention as described below.

We further provide a polypeptide, which can be obtained by the method according to the invention as described below and which comprises an N-glycosylated carbohydrate chain.

We also disclose the use of at least one polypeptide for the preparation of a therapeutic composition.

DETAILED DESCRIPTION

A method of producing at least one polypeptide from the nuclear genome of *Ostreococcus* sp. is disclosed. The method comprises:
 (i) introducing at least one recombinant nucleic acid molecule into the nuclear genome of *Ostreococcus* sp., wherein the recombinant nucleic acid molecule comprises a first polynucleotide operatively linked to a second polynucleotide,
wherein the second polynucleotide encodes at least one polypeptide and
 wherein the first polynucleotide comprises a promoter sequence allowing expression of said at least one polypeptide in *Ostreococcus* sp.

The use of *Ostreococcus* sp. to express a polypeptide or a protein complex according to our methods provides the advantage that a polypeptide or a protein complex can be expressed from the nuclear genome, thus allowing for correct expression of a desired product without genetically modify each codon of a gene, contrary to the *Chlamydomonas reinhardtii* plastidial expression system.

The term "polypeptide" is used herein to refer to a linear series of amino acid residues connected to one another by peptide bonds between the alpha amino group and carboxy group of contiguous amino acid residues.

As used herein, the term "*Ostreococcus* sp." refers to the unicellular green algae sp. of the Prasinophyceae family. According to the invention, the *Ostreococcus* sp. can be chosen from the group comprising *Ostreococcus tauri*, available at the Culture Collection of Algae and Protozoa (CCAP) in the United Kingdom (SAMS Research Services Ltd. OBAN, Argyll PA37 IQA, Scotland) with the accession number given by the International Depositary Authority CCAP 157/1, *Ostreococcus oceanica*, *Ostreococcus* sp. available at the Roscoff Culture Collection of Marine Phytoplankton (RCC) at Roscoff in France under the references RCC141, RCC143, RCC343, RCC344, RCC356, RCC371, RCC371, RCC393, RCC410, RCC420 and RCC501, preferably *Ostreococcus tauri*.

For example, the wild type strain 0TTH0595 of *Ostreococcus tauri* is available at the Roscoff Culture Collection of Marine Phytoplankton (RCC) at Roscoff in France with the reference RCC 614 or at the Culture Collection of Algae and Protozoa (CCAP) in the United Kingdom (SAMS Research Services Ltd. OBAN, Argyll PA37 IQA, Scotland) with the accession number given by the International Depositary Authority CCAP 157/1. Its entire genome is available under the following EMBL accession numbers: CR954201 (Chrom 1); CR954202 (Chrom 2); CR954203 (Chrom 3); CR954204 (Chrom 4); CR954205 (Chrom 5); CR954206 (Chrom 6); CR954207 (Chrom 7); CR954208 (Chrom 8); CR954209 (Chrom 9); CR954210 (Chrom 10); CR954211 (Chrom 11); CR954212 (Chrom 12); CR954213 (Chrom 13); CR954214 (Chrom 14); CR954215 (Chrom 15); CR954216 (Chrom 16); CR954217 (Chrom 17); CR954218 (Chrom 18); CR954219 (Chrom 19); CR954220 (Chrom 20). The use of *Ostreococcus* sp. to express a polypeptide according to our method of the invention provides the advantage that its genetic code is not biaised, all codons being present, thus facilitating the expression and production of polypeptide.

A method of introducing at least one recombinant nucleic acid molecule into *Ostreococcus* sp. can be easily identified by one skilled in the art regarding to their general knowledge. For example, the step (i) of introducing can be performed by electroporation.

The term "recombinant nucleic acid molecule" is used herein to refer to a polynucleotide, which can be resulted from experimental recombination.

The term "polynucleotide" is used herein to mean a sequence of two or more deoxyribonucleotides or ribonucleotides that are linked together by a phosphodiester bond. As such, the term includes RNA and DNA, preferably DNA, which can be a gene or a portion thereof, a cDNA, a synthetic polydeoxyribonucleic acid sequence, or the like, and can be single stranded or double stranded, as well as a DNA/RNA hybrid. Furthermore, the term as used herein include naturally occurring nucleic acid molecules, which can be isolated from a cell, as well as synthetic polynucleotides, which can be prepared, for example, by methods of chemical synthesis or by enzymatic methods such as by the polymerase chain reaction (PCR).

As used herein, the term "operatively linked" means that two or more molecules can be positioned with respect to each other such that they act as a single unit and effect a function attributable to one or both molecules or a combination thereof. For example, a polynucleotide encoding a polypeptide can be operatively linked to a transcriptional or translational regulatory element, in which case the element confers its regulatory effect on the polynucleotide similarly to the way in which the regulatory element would effect a polynucleotide sequence with which it is normally associated with in a cell.

As used herein, the term "promoter sequence" refers to a DNA region comprising a binding site of RNA polymerase as well as at least a binding site of transcription regulatory proteins. A promoter sequence useful for the invention can be easily identified by one skilled in the art with their general knowledge. For example, the promoter sequence useful for the invention can be chosen from the group comprising the *Ostreococcus tauri* histone H4 promoter sequence (identified by SEQ ID No 1), the *Ostreococcus tauri* cpx promoter sequence (identified by SEQ ID No 5), the *Ostreococcus tauri* crd1 promoter sequence (identified by SEQ ID No 4), the *Ostreococcus tauri* high affinity phosphate transporter (HAPT) promoter (identified by SEQ ID No 3). Particularly, the promoter sequence according to the invention can comprise SEQ ID No 3.

The method can be performed, wherein the second polynucleotide comprises at least one exogenous nucleotide sequence coding at least one polypeptide. As used herein, the term "exogenous nucleotide sequence" refers to a nucleotide sequence, which is not naturally found in the *Ostreococcus* sp. genome. Furthermore, the term as used herein includes naturally occurring nucleotide sequence, as well as synthetic nucleotide sequence, genomic DNA sequence, cDNA sequence and RNA sequence, preferably DNA sequence. For example, in the method, the at least one exogenous nucleotide sequence can be a marker gene. The term "marker gene" as used herein, refers to a polynucleotide that confers a detectable phenotype. A marker gene can be easily identified by one skilled in the art regarding to their general knowledge. Particularly, a marker gene can be chosen from the group comprising genes inducing resistance to antibiotic like G418 (e.g. KanMx identified by SEQ ID No 6) or nourseothricin acetyltransferase (e.g. Nat1 identified by SEQ ID No 9), and reporter genes like firefly luciferase or renilla genes producing luminescence upon hydrolysis of their substrate luciferin and coelenterazin respectively. Particularly, the at least one exogenous nucleotide sequence according to the invention can be a sequence of therapeutic interest. A sequence of therapeutic interest can be easily identified by one skilled in the art according to its general knowledge. For example, a sequence of therapeutic interest can be a wild type gene, which could be non functional gene in a particular pathology, a negative mutant of a gene, a sequence coding for a functional inhibitor of a gene. Particularly, a sequence of therapeutic interest can be a gene coding for a glycoprotein like an allergen, such as an acarian allergen.

The method of the invention can be practiced, wherein the second polynucleotide encodes a first polypeptide and at least a second polypeptide. Any or all of the encoded polypeptides can be the same or different. As such, the method provides a means to produce functional protein complexes, including, for example, dimers, trimers, and tetramers, wherein the subunits of the complexes can be the same or different. Particularly, the first polypeptide and the at least second polypeptide can correspond to a fusion protein. As used herein, the term "fusion protein" refers to a polypeptide produced by recombinant DNA methods in which a first polypeptide domain is operatively linked to a second polypeptide domain by the peptide bond produced through expression of a single open reading frame to express a single "fused" polypeptide. Particularly, the fusion protein can contains a peptide tag such as a His-6 tag, a "FLAG-epitope", a biotin or the like, which can facilitate identification or expression of the fusion protein in a cell. Such tags can provide the advantage that they can facilitate isolation of the fusion protein, for example, when it is desired to obtain a purified protein.

Particularly, the first polypeptide can comprise an immunoglobulin heavy chain (H) or a variable region thereof ($V_H$), and the second polypeptide can comprise an immunoglobulin light chain (L) or a variable region thereof ($V_L$). An immunoglobulin heavy chain can associate with an immunoglobulin light chain to form a monovalent antibody in *Ostreococcus* sp., and two monovalent antibodies can further associate to produce bivalent antibody. As such, the method provides a mean to produce functional protein complexes such as antibodies.

The method can be performed, wherein the second polynucleotide consists of 0.5 to 10 kb, preferably of 0.5 to 5 kb and, more preferably, of 0.5 to 3 kb.

Particularly, the second polynucleotide can comprises a "target signal". As used herein, the term "target signal" refer to a nucleotide sequence that targets a polypeptide to a particular location regarding to the cell, for example, to the cytosol, nucleus, plasma membrane, endoplamic reticulum, to an extracellular medium (i.e., secretion). Particularly, the second polynucleotide can comprises a secretion signal allowing secretion of the at least one polypeptide in *Ostreococcus* sp. A secretion signal can be easily identified by one skilled in the art. For example, the secretion signal is chosen from the group comprising the *Ostreococcus tauri* predicted aqualysin/subtilisin secreted protease sequence peptide (i.e. MRRFLTTVVLTACVSRANAF corresponding to SEQ ID No 17). The use of *Ostreococcus* sp. to express a polypeptide or protein complex according to the method provides the advantage that *Ostreococcus* sp. have no cell wall, thus allowing for production of secreted proteins and facilitating the purification of proteins.

The method can further comprise:

(ii) harvesting the at least one polypeptide expressed in *Ostreococcus* sp.

As used herein, the term "harvesting" means that a polypeptide is isolated from *Ostreococcus* sp. Particularly, the at least one polypeptide can be substantially purified which means that it is relatively free of proteins, nucleic acids, lipids, carbohydrate or other with which it is naturally associated. Generally, a substantially purified polypeptide constitutes at least about fifty percent, particularly about eighty percent of a sample.

*Ostreococcus* sp. can be grown in a bioreactor. The bioreactor can be easily identified by one skilled in the art regarding their general knowledge, for example, Labfors-lux (Infors HT).

Particularly, *Ostreococcus* sp. can be grown in a culture medium comprising at least one compound stimulating the grow of *Ostreococcus* sp. A compound stimulating the growth of *Ostreococcus* sp. can be easily identified by one skilled in the art regarding to their general knowledge. For example, the at least one compound stimulating the growth of *Ostreococcus* sp. can be chosen from the group comprising nitrate, ammonium, phosphate and carbon dioxide. The use of *Ostreococcus* sp. to express a polypeptide or a protein complex according to the methods provides the advantage that large populations of *Ostreococcus* sp. can be grown, thus allowing for production and if desired, isolation of large amounts of a desired product.

*Ostreococcus* sp. can be grown in a culture medium comprising at least one beta 1,4 galactosyl transferase. The use of *Ostreococcus* sp. to express a polypeptide or a protein complex according to the methods provides the advantage that a polypeptide or a protein complex can be expressed from the nuclear genome, thus allowing for glycosylation of a desired product, contrary to the *Chlamydomonas reinhardtii* plastidial expression system.

Moreover, some in silico and immunochemical data suggest that the glycosylation of protein in *Ostreococcus* sp. differs from that in the higher plants with in particular the absence of immunogenic and allergenic residues like beta 1,2 xylose and alpha 1,3 fucose. Thus, the use of *Ostreococcus* sp. to express a polypeptide or a protein complex according to methods of the invention provides the advantage that the glycosylation does not provide immunogenic and allergenic residues like beta 1,2 xylose and alpha 1,3 fucose, thus allowing for glycosylation of a desired product without allergenic residues.

We also provide an expression cassette for expression of at least one polypeptide in *Ostreococcus* sp., wherein the cassette comprises:

(a) a promoter sequence operatively linked to and positioned upstream of a cloning site for insertion of a nucleotide sequence coding for said at least one polypeptide, wherein the promoter sequence allows expression of said at least one polypeptide in *Ostreococcus* sp.

As used herein, the term "upstream" refers to the direction opposite to the direction of DNA transcription, and therefore going from 5' to 3' on the noncoding strand, or 3' to 5' on the RNA transcript.

As used herein, the term "cloning site" is used broadly to refer to any nucleotide or nucleotide sequence that facilitates linkage of a first polynucleotide to a second polynucleotide. For example, a cloning site can be chosen from the group comprising at least one restriction endonuclease recognition site like multiple cloning site, at least one recombinase recognition site like a loxP site.

A promoter sequence can be easily identified by one skilled in the art with his general knowledge. For example, the promoter sequence can be chosen from the group comprising the *Ostreococcus tauri* histone H4 promoter sequence (identified by SEQ ID No 1), the *Ostreococcus tauri* cpx promoter sequence (identified by SEQ ID No 5), the *Ostreococcus tauri* crd1 promoter sequence (identified by SEQ ID No 4), the *Ostreococcus tauri* high affinity phosphate transporter (HAPT) promoter (identified by SEQ ID No 3). Particularly, the promoter sequence can comprise SEQ ID No 3.

We also provide a vector comprising at least one expression cassette according to the invention. The vector can be any vector useful for introducing a polynucleotide into a prokaryotic or eukaryotic cell, including a cloning vector or an expression vector. In one embodiment, the vector can further comprise a prokaryotic origin replication. Particularly, the origin of replication can be an *E. Coli* origin replication. As such, a vector can be passaged and manipulated in a prokaryote host cell as well as in *Ostreococcus* sp. The vector can further comprise at least one cloning site and/or one regulatory element and/or at least one marker gene and/or at least one target signal.

As used herein, the terms "regulatory element" refers to a nucleotide sequence which regulates the transcription or translation of a polynucleotide to which it is operatively linked.

We also provide a cell, which can be obtained by the method. Particularly, the cell can be an *Ostreococcus* sp. cell. The *Ostreococcus* sp. can be chosen from the group comprising *Ostreococcus tauri*, available at the Culture Collection of Algae and Protozoa (CCAP) in the United Kingdom (SAMS Research Services Ltd. OBAN, Argyll PA37 IQA, Scotland) with the accession number given by the International Depositary Authority CCAP 157/1, *Ostreococcus oceanica*, *Ostreococcus* sp., available at the Roscoff Culture Collection of Marine Phytoplankton (RCC) at Roscoff in France under the references RCC141, RCC143, RCC343, RCC344, RCC356, RCC371, RCC371, RCC393, RCC410, RCC420 and RCC501, preferably *Ostreococcus tauri*. Particularly, the cell according to the invention can be the *Ostreococcus tauri* cell registered with the RCC under No RCC 614 or available at the Culture Collection of Algae and Protozoa (CCAP) in the United Kingdom (SAMS Research Services Ltd. OBAN, Argyll PA37 IQA, Scotland) with the accession number given by the International Depositary Authority CCAP 157/1.

We also provide a polypeptide, which can be obtained by the method and which can comprises an N-glycosylated carbohydrate chain. In one embodiment, the polypeptide is a single chain antibody. As such, the method provides a mean to produce functional protein complexes such as antibodies, which are N-glycosylated.

We also provide a pharmaceutical composition comprising at least one polypeptide.

We further provide the use of at least one polypeptide for the preparation of a therapeutic composition. Particularly, the therapeutic composition can be for the treatment of a disease chosen from the group comprising cancers, infectious diseases, cardiovascular diseases, neurodegenerative diseases like Alzheimer or Parkinson diseases, genetic diseases like monogenic genetic diseases.

Selected, representative aspects of the disclosure will now be illustrated by the following non-limiting examples.

BRIEF DESCRIPTION OF THE FIGURES

FIG. 3 shows the measure of the luciferase luminescence on protein extracts from 34 different *Ostreococcus tauri* transformants (grey and white boxes). These cells were transformed by a DNA carrying resistance to G418 and the luciferase+gene fused to the whole gene PRR1 of *Ostreococcus tauri*. In black box, the negative control (no DNA). In grey box, the luminescence, which was two times higher than the negative control. In white box, the luminescence, which was two times less than negative control.

FIG. 6 (A to D) show the optimization of *Ostreococcus tauri* cells transformation by electroporation by testing different conditions.

EXAMPLES

Example 1

Expression of a Luciferase Fusion Protein in *Ostreococcus tauri*

This example demonstrates the expression of a luciferase fusion protein in *Ostreococcus tauri*.
Methods
Preparation of Ostreococcus Tauri Competent Cells.

The wild type strain 0TTH0595 of *Ostreococcus tauri* was used to prepare competent cells. These cells are available at the Roscoff Culture Collection of Marine Phytoplankton (RCCMP) at Roscoff in France with the reference RCC 614 and at the Culture Collection of Algae and Protozoa (CCAP) in the United Kingdom (SAMS Research Services Ltd. OBAN, Argyll PA37 IQA, Scotland) with the accession number given by the International Depositary Authority CCAP 157/1. The whole preparation of *Ostreococcus tauri* competent cells was carried out in sterile conditions. The cells of *Ostreococcus tauri* (wild type strain 0TTH0595) were grown in blue light (30 mmol quanta cm$^{-2}$ second$^{-1}$) at 20° C. until a density of 30 million cells per ml. The culture medium comprising seawater added with Keller Medium from Sigma-Aldrich (reference: K1630) was filtered on 0.22 μm and autoclaved. After addition of pluronic acid F-68 to 0.1% w/vol final (Sigma Aldrich, reference: P7061), the cells were harvested in conical tubes of 50 ml (Sarstedt), by centrifugation at 8000×g at 4° C. for 8 min. The protocol was then carried out on ice. Salts are washed out from the cells by two washes with 1 ml of 1M sorbitol (10 000 g, 5 min, 4° C.). Cells were resuspended in 50 μl 1M sucrose to a final concentration of 2 to 3·10$^{10}$ cells per ml.
Plasmid Construction Three types of fusion were prepared:
 fusion of an antibiotic resistance gene to the *Ostreococcus tauri* histone H4 promoter (G418 resistance gene: PotLuc vector and clonat resistance gene: pH4Nat1 vector);
 fusion of the HAPT Promoter to the firefly luciferase gene (PotLuc-HAPT vector);
 fusion of the PPR1 (Pseudo Response Regulator 1) gene of *Ostreococcus tauri* to the firefly luciferase gene (PotLuc-PPR1 vector).

All DNA manipulations were carried out essentially as described by Sambrook et al. (*Molecular cloning. A laboratory Manual* Cold Spring Harbor Laboratory Press, 1989). The *Ostreococcus tauri* histone H4 promoter corresponds to a DNA fragment of *Ostreococcus tauri* amplified by PCR by using the two primers ot-H4 For and ot-H4 Rev. The sequence for ot-H4 For is 5'-GCG GAT CCC ACG GAG CGC AAC GGT ACC-3' (SEQ ID No: 13); the sequence for ot-H4 Rev is 5'-CC AGC GCC AGC CAT GGT TTT CGA ACG-3' (SEQ ID No: 14).

The TEF promoter of the PAG25 vector (SEQ ID No 11) encoding the nourseothricin acetyltransferase (Clonat) resistance gene (Nat1) was replaced by the *Ostreococcus tauri* Histone H4 promoter using the BamHI and NcoI sites.

Figure 1:
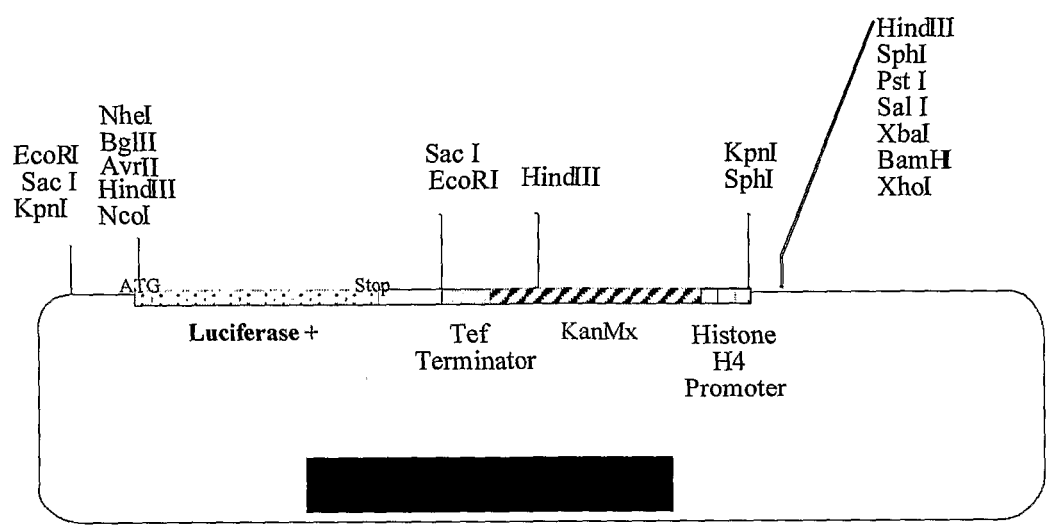
FIG. 1 provides a map of the PotLuc vector, showing relevant restriction sites, the G418 resistance gene (KanMx) under control of the Histone H4 promoter of *Ostreococcus tauri* followed by the TEF terminator and the luciferase+ gene.

The *Ostreococcus tauri* histone H4 promoter was fused to the G418 antibiotic resistance gene of KanMx module (Genbank accession number S78175) between the sites BamHI and NcoI from PUG6.5 (to replace the TEF promoter). The obtained plasmid was named PotH4KanMx. The luciferase+ gene from pSP-luc+NF of Promega was inserted into PotH4KanMx using the sites XbaI and NheI. The resulting plasmid, named Potluc makes it possible to fuse genes to the luciferase+gene. The Potluc plasmid has a replication origin for *E. coli* and an ampicillin resistance gene already present in pUC 19. The Potluc plasmid has also a gene coding for the firefly luciferase gene (SEQ ID No 10), as well as a G418 resistance gene (SEQ ID No 6) used as a selection marker in *Ostreococcus tauri* under control of the strong promoter of the *Ostreococcus tauri* histone H4 (SEQ ID No 1), and followed by the TEF terminator (SEQ ID No 7) (FIG. 1).

Figure 2A:
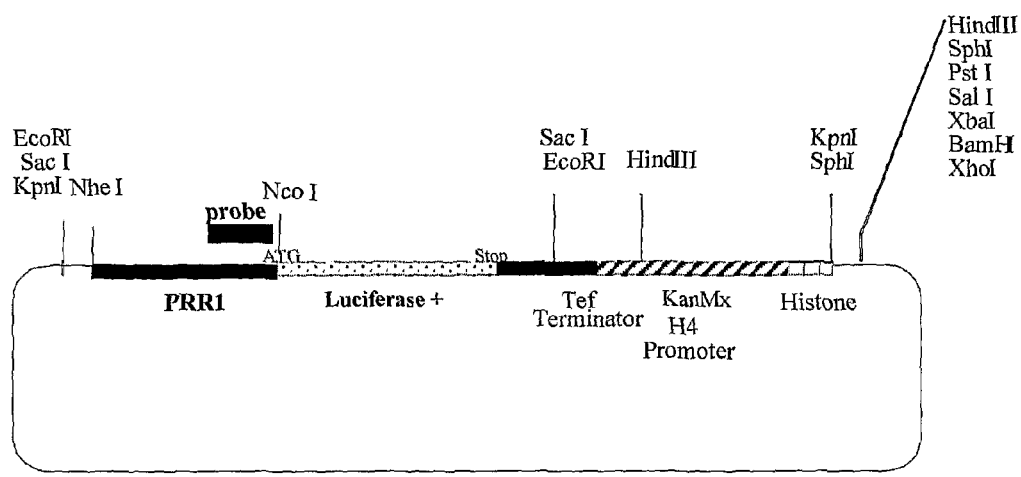
FIG. 2A provides a schema of the fusion of the PRR1 gene of *Ostreococcus tauri* to a luciferase gene in PotLuc, to generate the PotLuc-PRR1 vector. Double heachures indicate regions corresponding to probe used in the Southern blot analysis.

The whole *Ostreococcus tauri* gene PRR1 (SEQ ID No 2) comprising 200 nucleotides of the promoter region was amplified by using the specific primers TOC1fullfuRNco1 and TOC1fullFNhe1 and was cloned between the sites NheI and NcoI of PotLuc, to generate plasmid PotLuc-PRR1 (FIG. 2A). The sequence of TOC1fullfuRNco1 is TTTCCATG-GACTTGGAGCCGTCGCGAGA (SEQ ID No: 15) and the sequence of TOC1fullFNhe1 is TTTGCTAGCACCTC-GAGCCGGGACCAAAAA (SEQ ID No: 16).

Figure 2B:
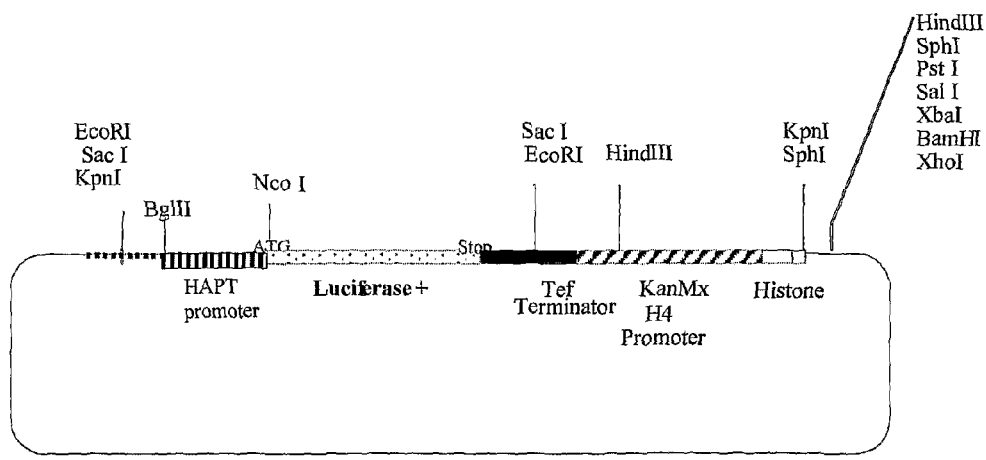
FIG. 2B provides a schema of the fusion of the HAPT (High Affinity Phosphate Transporter) promoter of *Ostreococcus tauri* to a luciferase gene in PotLuc, to generate the PotLuc-HAPT vector.

The HAPT promoter (SEQ ID No 3) consisting of 100 by upstream of the ATG, was cloned into Potluc between the BglII and NcoI sites, to generate plasmid PotLuc-HAPT (FIG. 2B).

DNA Preparation for *Ostreococcus tauri* Transformation

The four DNA constructs were linearized using an accurate restriction enzyme that cuts upstream of promoters driving the expression of the different genes of interest: the *Ostreococcus tauri* histone H4 promoter fused to the Clonat resistance; the *Ostreococcus tauri* histone H4 promoter fused to the G418 resistance; the *Ostreococcus tauri* histone H4 promoter fused to the G418 resistance gene followed by either the *Ostreococcus tauri* PRR1 gene or HAPT promoter fused to the luciferase gene. Linearized plasmids were purified by ethanol precipitation after tRNA addition (1 mg/ml final concentration) (Sigma-Aldrich, RS636) and resuspended in water to obtain a final DNA concentration of 1 µg/µl.

*Ostreococcus tauri* transformation by electroporation was optimized as shown in FIG. 6. The linearized DNA construct issued from the PotLuc-HAPT plasmid (by XmnI) containing the HAPT promoter (strong promoter) fused to the luciferase (ca 6 kb) was used to optimize electroporation conditions by monitoring the luciferase activity. The experimental conditions described below are those with the highest transformation efficiency and the highest viability (Sorbitol buffer, Field strength 600V/cm, resistor 400Ω. For one transformation, 50 ml of competent cells ($2 \cdot 10^{10}$ cells) prepared as described above were incubated with 5 µl of DNA on ice for at least 10 min and transferred to in a 1 mm electroporation cuvette and left to warm up at RT for ca 2 min (Bridge Biosciences). Electroporation was performed in a Gene pulser apparatus (Biorad) with the following electrical parameters: Field strength 600V/cm, resistor 400Ω Capacitor 25 µF. Time constant was between 8 and 9 ms. The electroporated cells were resuspended in 40 ml of culture medium as described in paragraph [0053] during 2 days (expression phase). After 48 hours, transformed cells were selected in a solid medium (Keller Medium (SIGMA Aldrich reference number K1630) containing 0.2% of agarose and the appropriate selection antibiotic). The solid medium was prepared as follows: the autoclaved low melting agarose (Invitrogen) at 2.1% w/v was maintained at 90° C. and was mixed at a rate of 1 Vol. for 9 Vol. of culture medium. 500 µl to 1 ml of transformed cells were mixed with ten milliliters of this medium and the mixture was poured on a Petri dish. Petri dishes were placed in a wet chamber under the same conditions of illumination as previously described.

Optimisation of *Ostreococcus* Cells Transformation by Electroporation

The linearized DNA construct (with XmnI) containing the high affinity phosphate transporter (HAPT) promoter fused to luciferase+(ca 6 kb) was electroporated in different conditions. Transient expression of the luciferase gene under the strong homologous promoter of HAPT was checked in the electroporated cells after one day. Luminescence signal per $10^6$ viable cells is normalized throughout different experiment as the percentage of the maximum signal (in Black). Mortality was defined by the percentage of cells with a low red fluorescence as assessed by flow cytometry after one day (In White). Results are shown in FIG. 6 (A to D).

Figure 6A:
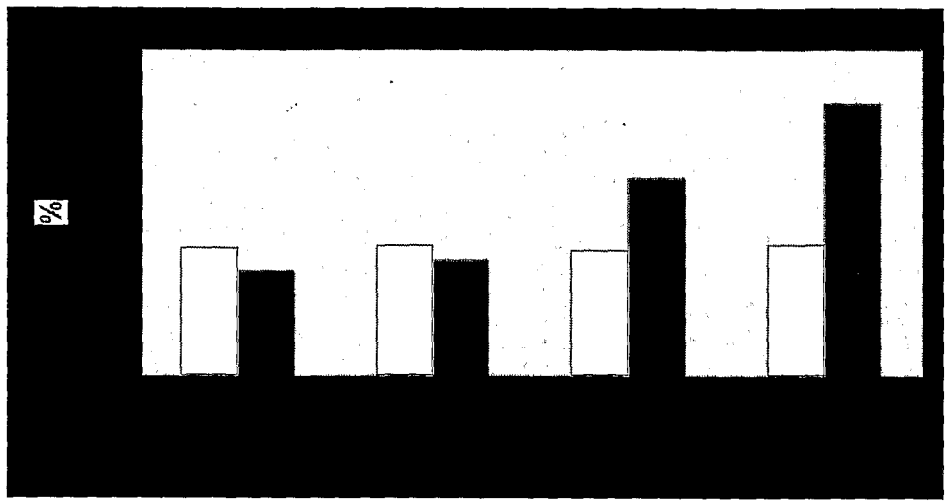
FIG. 6A shows the effect of the osmoticum.

FIG. 6A shows the effect of the osmoticum. Cells were resuspended either in 1M sucrose or 1M sorbitol and electroporated at 800V/cm 200Ω and 400Ω (25 µF) to increase the time constant. The viability was equivalent in both osmoticum but transformation efficiency was higher in sorbitol, notably for higher time constant and was therefore used for further optimization.

Figure 6B:
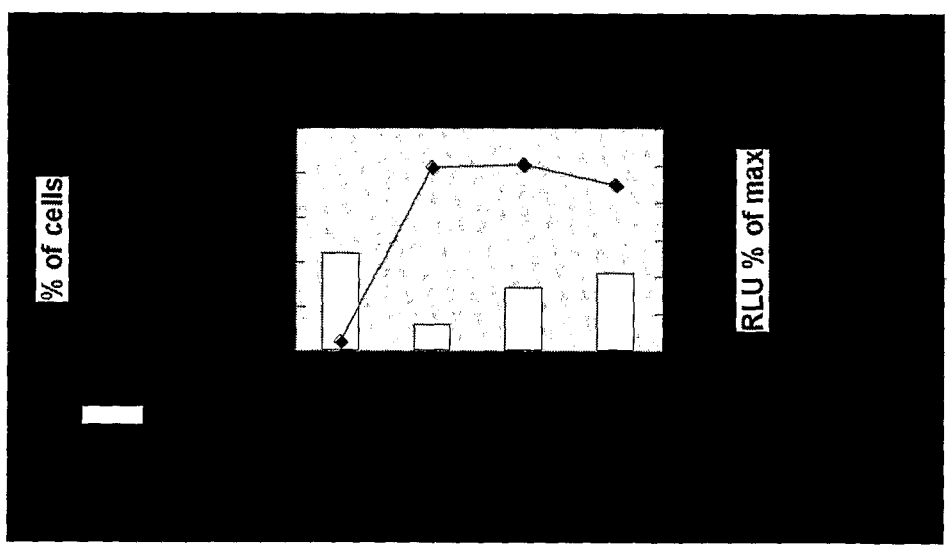
FIG. 6B shows the effect of the pulse duration.

FIG. 6B shows the effect of the pulse duration. Cells were electroporated at 800V/cm and the resistance was adjusted to increase the pulse duration (time constant). Transformation efficiency was greatly improved for constant time above 5 ms while viability was about 80% in this experiment.

Figure 6C:
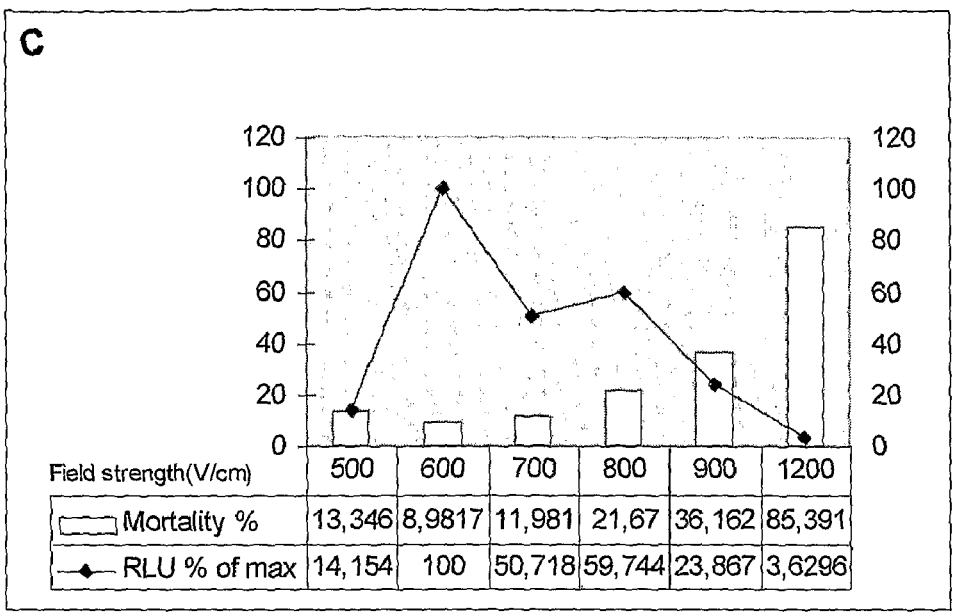
FIG. 6C shows the effect of the field strength.

FIG. 6C shows the effect of field strength. Electroporation was almost inefficient at 500V and was maximal at 600V still efficient but reduced by ca 50% until 800 V. Voltage above greatly affected cell viability and probably thereby decreased efficiency.

Figure 6D:
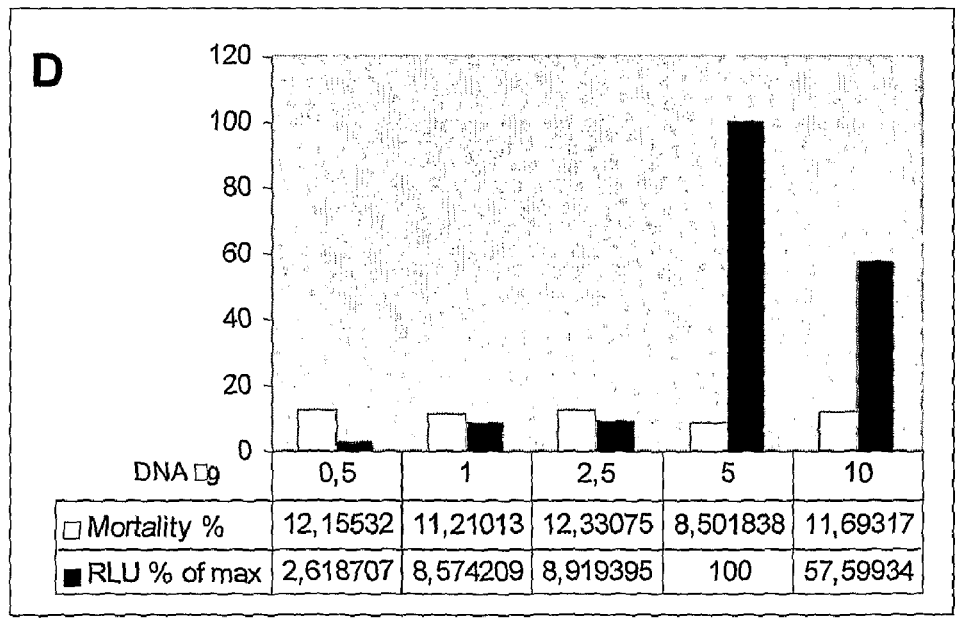
FIG. 6D shows the effect of the DNA quantity.
Figure 7:
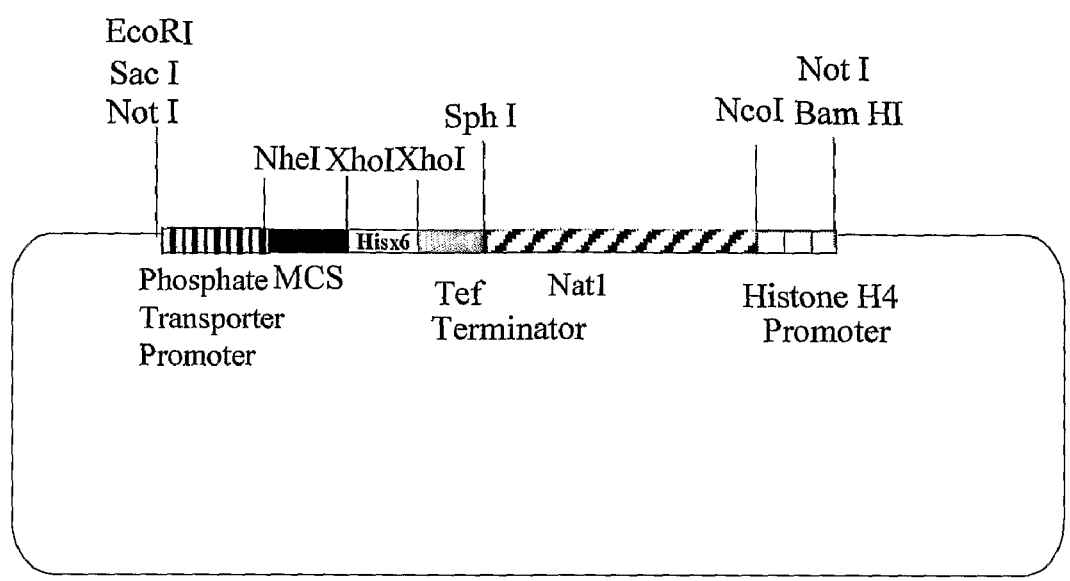
FIG. 7 provides a map of the Potox vector showing relevant restriction sites, the Nourseothricin acetyltransferase resistance gene (Nat1) under control of the Histone H4 promoter of *Ostreococcus tauri* followed by the Tef terminator, a 6× histidine Tag, a multiple cloning site (MCS) and the phosphate transporter promoter.

FIG. 6D shows the Effect of DNA quantity (concentration of 1 mg/ml). The Optimal quantity of DNA was 5 µg.

Results:

Stable *Ostreococcus tauri* Transformants which are Resistant to Antibiotics

*Ostreococcus tauri* cells were transformed by the linearized PotLuc plasmid (by XmnI) carrying resistance to G418 under control of the *Ostreococcus tauri* histone H4 promoter. Four independent transformations were carried out. The positive clones were selected on G418 at 1 mg/ml. 50 to 1000 transformants were obtained per microgram of DNA. No transformants were obtained in the negative controls electropored under the same conditions without DNA. I. No transformants were obtained in the negative controls electropored under the same conditions without DNA.

*Ostreococcus tauri* cells were transformed by the linearized pH4Nat1 plasmid (by XmnI) carrying resistance to Clonat under control of the *Ostreococcus tauri* histone H4 promoter. Two independent transformations were carried out. The positive clones were selected on Clonat at 700 mg/ml. Up to 500 transformants were obtained per microgram of DNA.

This example shows that it is possible to use exogenous selection genes with no bias in codon usage in *Ostreococcus tauri*.

Expression of a Luciferase Recombinant Protein in *Ostreococcus tauri*

*Ostreococcus tauri* cells were tranformed by the linearized PotLuc-PRR1 plasmid (with NheI) carrying resistance to G418 and the luciferase+gene fused to the whole gene PRR1 of *Ostreococcus tauri* (FIG. 2A). 1000 transformants per microgram of DNA were obtained on the basis of selection into G418 1 mg/ml, which is the lethal dose for wild type *Ostreococcus tauri*. Luminescence was measured using a luminometer Berthold LB 360, in the presence of luciferin, either directly on the cultures into microplaques or on protein extract (FIG. 3).

Figure 4A:
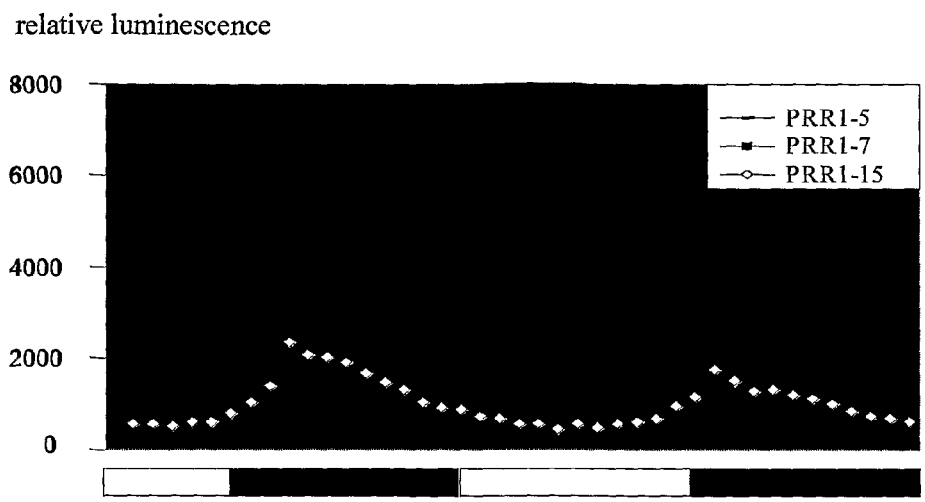
FIG. 4A shows the luciferase activity of three different *Ostreococcus tauri* stable transformants (PRR1-5, PRR1-7 and PRR1-15). These cells were transformed by a DNA carrying resistance to G418 and the luciferase+gene fused to the whole gene PRR1 of *Ostreococcus tauri*. These transformants were cultivated in alternation day/night (White box/black box).
Figure 4B:
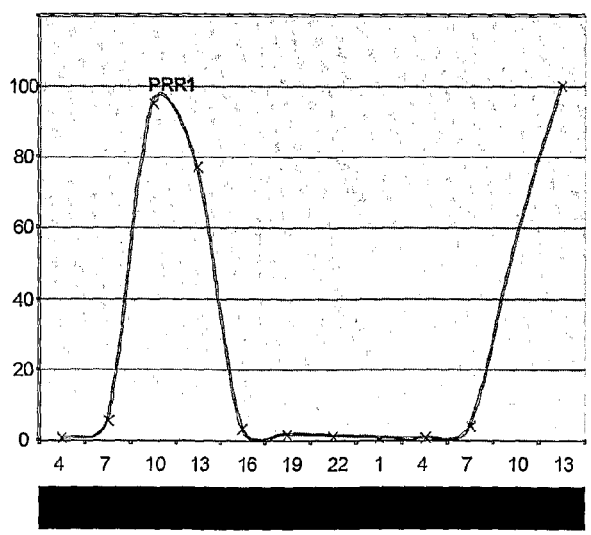
FIG. 4B shows the expression of PRR1 mRNA measured with quantitative RT-PCR and regarding to EF1α, control cells.
Figure 5:
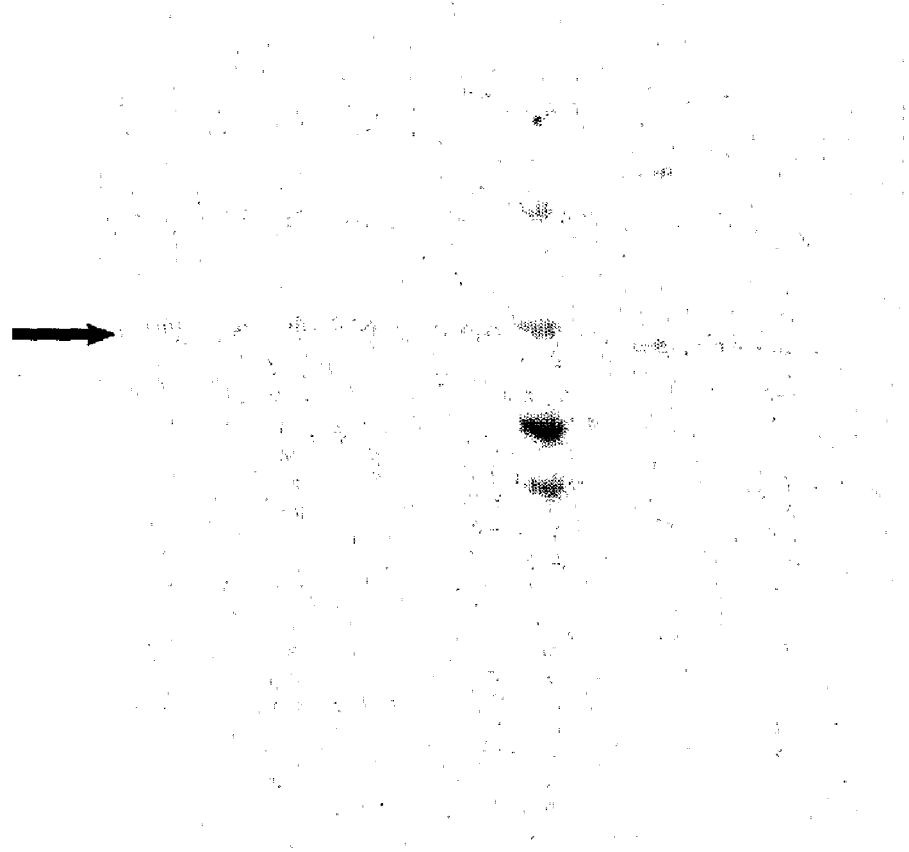
FIG. 5 shows the detection of the insertion of the gene PRR1 by Southern-Blot in 10 different transformants resistant to G418 and which present a luciferase activity. Lines 1, 5 and 7 correspond to the transformants PRR1-5, PRR1-7 and PRR1-15. Line C corresponds to the negative control which was not transformed. The used probe corresponds to the 3' region of the PRR1 gene (600 pb) as described in FIG. 2A.

The results show that more than 90% of the tested clones had luciferase levels higher than transformed negative control which were transformed without DNA (2 to more 100 000 times). The luciferase activity of different transformants were tested in vivo on 200 µl of culture cells at $3 \cdot 10^7$ cells/ml incubated in the presence of luciferine 200 µM, cultivated in alternation day/night (FIG. 4A). Similar profiles of cyclic expression of luciferase were observed in these various clones. These profiles reflect the expression of PRR1 mRNA measured with quantitative RT-PCR (FIG. 4B), which suggests that the PRR1 gene is entirely inserted. DNA of 10 transformants were extracted (Kit Dneasy Plant mini Kit from Qiagen), digested by the enzyme of restriction NcoI and used for Southern Blot. A probe corresponding to 600 pb of the 3' coding region of PRR1 was used to detect insertions of the construction in the genome of *Ostreococcus tauri* (FIG. 5).

The results show that the presence of endogenous gene PRR1 in wild type strain 0TTH0595 (C) was detected by an hybridization signal at 4 kb. This band was found in all transformants. Supernumerary bands correspond to multiple insertions (1 to 3). On average, 2 events of integration by transformants were observed.

Different transformants accumulated the luciferase at various levels of expression. The analysis of transformants showed multiple events of integration in the genome and suggested that the introduced fragments were not truncated since more than 90% of the cells resistant to G418 presented an expression of luciferase reflecting the expression of gene PRR1.

This example shows the efficiently of the expression of the recombinant protein luciferase+in *Ostreococcus tauri*.

Example 2

Construction of the Potox Vector

The TEF promoter upstream of the Nat1 coding sequence in the PAG25 vector was replaced by the histone H4 promoter from *Ostreococcus* between BamHI and NcoI cloning sites. A synthetic multiple cloning site (MCS) followed by a sequence encoding a 6× histidine tag and is complementary sequence (SEQ ID No 17 and SEQ ID No 18) were subsequently introduced together with the *Ostreococcus tauri* HAPT promoter, generating the Potox vector. This vector allows to clone and express the coding sequence of interest under control of the strong HAPT promoter. The transformants can be selected on the basis of CLONAT resistance at 750 µg/ml. The protein of interest can be purified using a 6× histidine TAG. This TAG can be removed, if required, using the Xho I restriction nuclease.

All documents referenced in this application, including those listed above, are herein incorporated by reference in their entirety. A variety of modifications to the embodiments described above will be apparent to those skilled in the art from the disclosure provided herein. Thus, the technology in this disclosure may be embodied in other specific forms without departing from the spirit or essential attributes thereof.

What is claimed is:

1. A method of producing at least one polypeptide from the nuclear genome of *Ostreococcus* sp., the method comprising: (i) introducing at least one recombinant nucleic acid molecule into the nuclear genome of *Ostreococcus* sp., wherein said recombinant nucleic acid molecule comprises a first polynucleotide operatively linked to a second polynucleotide, wherein said second polynucleotide encodes at least one polypeptide and wherein said first polynucleotide comprises a promoter sequence allowing expression of said at least one polypeptide in *Ostreococcus* sp.

2. The method according to claim 1, wherein the *Ostreococcus* sp. is at least one chosen from the group consisting of *Ostreococcus* sp. available at the Roscoff Culture Collection of Marine Phytoplankton (RCC) at Roscoff in France under the references RCC141, RCC143, RCC343, RCC344, RCC356, RCC371, RCC371, RCC393, RCC410, RCC420 and RCC501 and *Ostreococcus tauri* available at the Culture Collection of Algae and Protozoa (CCAP) in the United Kingdom (SAMS Research Services Ltd. OBAN, Argyll PA37 IQA, Scotland) with the accession number given by the International Depositary Authority CCAP 157/1.

3. The method according to claim 1, wherein the *Ostreococcus* sp. is *Ostreococcus tauri* available at the Culture Collection of Algae and Protozoa (CCAP) in the United Kingdom (SAMS Research Services Ltd. OBAN, Argyll PA37 IOA, Scotland) with the accession number given by the International Depositary Authority CCAP 157/1.

4. The method according to claim 1, wherein the promoter sequence is at least one chosen from the group consisting of the *Ostreococcus tauri* histone H4 promoter sequence (identified by SEQ ID No 1), the *Ostreococcus tauri* cpx promoter sequence (identified by SEQ ID No 5), the *Ostreococcus tauri* crd1 promoter sequence (identified by SEQ ID No 4), the *Ostreo-coccus tauri* high affinity phosphate transporter (HAPT) promoter (identified by SEQ ID No 3).

5. The method according to claim 4, wherein the promoter sequence comprises SEQ ID No 3.

6. The method according to claim 1, wherein the second polynucleotide comprises at least one exogenous nucleotide sequence coding at least one polypeptide.

7. The method according to claim 6, wherein said at least one exogenous nucleotide sequence is a marker gene which induces resistance to antibiotics.

8. The method according to claim 6, wherein said at least one exogenous nucleotide sequence is a sequence of therapeutic interest.

9. The method according to claim 1, wherein the second polynucleotide encodes a first polypeptide and at least a second polypeptide.

10. The method according to claim 9, wherein the first polypeptide and the at least second polypeptide correspond to a fusion protein.

11. The method according to claim 10, wherein the first polypeptide comprises an immunoglobulin heavy chain or a variable region thereof, and the second polypeptide comprises an immunoglobulin light chain or a variable region thereof.

12. The method according to claim 1, wherein the second polynucleotide consists of 0.5 to 10 kb.

13. The method according to claim 1, wherein the second polynucleotide comprises a secretion signal allowing secretion of the at least one polypeptide in *Ostreococcus* sp.

14. The method according to claim 13, wherein the secretion signal is *Ostreococcus tauri* predicted aqualysin/subtilisin secreted protease sequence peptide (SEQ ID No 17).

15. The method according to claim 1, wherein the step (i) of introducing is carried out by electroporation.

16. The method according to claim 1, further comprising: (ii) harvesting the at least one polypeptide expressed in *Ostreococcus* sp.

17. The method according to claim 1, wherein *Ostreococcus* sp. is grown in a bioreactor.

18. The method according to claim 1, wherein *Ostreococcus* sp. is grown in a culture medium comprising at least one compound stimulating the growth of *Ostreococcus* sp., wherein the at least one compound is at least one chosen from the group consisting of nitrate, ammonium, phosphate and carbon dioxide.

19. An expression cassette for expression of at least one polypeptide in *Ostreococcus* sp., wherein said cassette comprises: (a) a promoter sequence operatively linked to and positioned upstream of a cloning site for insertion of a nucleotide sequence coding for said at least one polypeptide, wherein the promoter sequence allows expression of the at least one polypeptide in *Ostreococcus* sp.

20. The expression cassette according to claim 19, wherein the promoter sequence is at least one chosen from the group consisting of the *Ostreococcus tauri* histone H4 promoter sequence (identified by SEQ ID No 1), the *Ostreococcus tauri* cpx promoter sequence (identified by SEQ ID No 5), the *Ostreococcus tauri* crdl promoter sequence (identified by SEQ ID No 4), the *Ostreococcus tauri* high affinity phosphate transporter (HAPT) promoter (identified by SEQ ID No 3).

21. The expression cassette according to claim 19, wherein the promoter sequence comprises SEQ ID No 3.

22. The expression cassette according to claim 19, wherein the cloning site is chosen from the group consisting of at least one restriction endonuclease recognition site and at least one recombinase recognition site.

23. A vector comprising at least one expression cassette according to claim 19.

24. The vector according to claim 23, further comprising a prokaryotic origin replication.

25. The vector according to claim 23, wherein the origin of replication is an *E. Coli* origin replication.

26. A cell comprising: (i) at least one recombinant nucleic acid molecule comprising a first polynucleotide operatively linked to a second polynucleotide, wherein said second polynucleotide encodes at least one polypeptide, and wherein said first polynucleotide comprises a promoter sequence allowing expression of said at least one polypeptide in *Ostreococcus* sp., wherein the cell is an *Ostreococcus* sp. cell chosen from the group consisting of *Ostreococcus tauri* available at the Culture Collection of Algae and Protozoa (CCAP) in the United Kingdom (SAMS Research Services Ltd. OBAN, Argyll PA37 IQA, Scotland) with the accession number given by the International Depositary Authority CCAP 157/1, *Ostreococcus oceanica*, *Ostreococcus* sp. available at the Roscoff Culture Collection of Marine Phytoplankton (RCC) at Roscoff in France under the references RCC141, RCC143, RCC343, RCC344, RCC356, RCC371, RCC371, RCC393, RCC410, RCC420 and RCC501, preferably *Ostreococcus tauri*.

27. The cell according to claim 26, which is the *Ostreococcus tauri* cell available at the Culture Collection of Algae and Protozoa (CCAP) in the United Kingdom (SAMS Research Services Ltd. OBAN, Argyll PA37 IQA, Scotland) with the accession number given by the International Deposit Authority CCAP 157/1.

28. The method of claim 2, wherein the *Ostreococcus* sp. is *Ostreococcus tauri*.

29. The method of claim 7, wherein the antibiotic resistance gene provides resistance to antibiotics chosen from the group consisting of G418 and nourseothricin acetyltransferase.

30. The method of claim 7, wherein the reporter gene is luciferase.

31. The method of claim 12, wherein the second polynucleotide consists of 0.5 to 5 kb.

32. The method of claim 12, wherein the second polynucleotide consists of 0.5 to 3 kb.

33. The method of claim 20, wherein the promoter sequence comprises SEQ ID No 3.

34. The method of claim 26, wherein the *Ostreococcus* sp. is *Ostreococcus tauri*.

* * * * *

SEQUENCE LISTING

<160> NUMBER OF SEQ ID NOS: 18

<210> SEQ ID NO 1
<211> LENGTH: 549
<212> TYPE: DNA
<213> ORGANISM: Ostreococcus tauri
<220> FEATURE:
<223> OTHER INFORMATION: Histone H4 promoter sequence

<400> SEQUENCE: 1

```
gcggatctca cggagcgcaa cggtacccgg gcggtacctg tgcggcttct tgacgccgcc      60
ggtcgccggg gcggacttgc gggccgcctt ggtggcgagt tgcttgcgcg gggccttgcc     120
accggtggac ttacgggcag tttgcttcgt acgggccata ttgactgtcg agttgtgacg     180
acgccgtgcg atcgaatcga gcgtttcacc gcgcgcgccg gtgagtcggt gagttcgaaa     240 gcaggggggtc atacacgagt cattactctc tatttacttg aaatgcccat ttttcacgtg     300
catgcatcac ttgattgttt ttaaatccac gcattgtggt tcatgactca ttgtgtgcca     360
tttagaaaca atcaacgcat caatgattgt gtgaaatgaa cttttttaccc ctataatttc     420 atgggtcgtg actcgcacgg agtattttca actcaccgcg aactcaccgg cgcccgcgtc     480
```

| | |
|---|---|
| cgtggccccg accgcgcgcg caggtcgtca ctaatcgaca cgttcgaaaa caacaatgtc | 540 |
| tggccgtgg | 549 |

<210> SEQ ID NO 2
<211> LENGTH: 2156
<212> TYPE: DNA
<213> ORGANISM: Ostreococcus tauri
<220> FEATURE:
<223> OTHER INFORMATION: PRR1 gene sequence

<400> SEQUENCE: 2

| | |
|---|---|
| acctcgagcc gggaccaaaa agcaaaaagc gaccacgggg tgtgccgaga tctcaaaaac | 60 |
| gaatcccgcg aaataccaca tttcatacat acacctacaa cacacacaat atgtatcaca | 120 |
| catccgatca aatatgttta tcgtgaaaat atctcaaaga cgatcacttt tcacccacct | 180 |
| cgcagctccc gtcgcggcgc cggcgcgagt gctccacgga cgccgcgcgc gtcgacgcgg | 240 |
| gcgacgcgcg atcgttcgcg agacgtcggc ggtgcgattg tctcttcgct ctcgtccgcg | 300 |
| ttcgatcgat cgagcgtcca gggaggcgga cgcgaggatt aatccaaacc atcgtttcct | 360 |
| cgacgcggcg accgggacgg cacagagacg ggacgggtct cgagacgcga gcgatgtccg | 420 |
| acgcgcgaac gcgctcgcga gggacggtgg acatcgatgg tgagacattg aagcgcgcgg | 480 |
| atcggggcg acggggcgt gaaagcgggg atcggcggag cgagacgaac gcggtggcgg | 540 |
| cggcgggaga ggacggcggc gagcgagacg cggacgcgct gcgagtcttg ctcgccacgg | 600 |
| atgacgcgca cacgcgagga atggtgcata aaatgttgag agagctcgga gtggaggttg | 660 |
| tgatggcgac gaacgggaaa gaggtcttgg aagttttgcg aggaaggccg aaaggcgtgg | 720 |
| cggcggcggc ggaggacgtt tcggtggaca tgattttgtt ggatgtgctc atgcccgctt | 780 |
| tggacggcga ggtcgagctc gtggaggtgt gcaagtcgaa tgaagcttta cgaggcgttc | 840 |
| ccattgttat catgtccacc gtggacgagc ggaaggcgtg cgggacgcgg tacgagcatt | 900 |
| ccggcgccgc tggtttcctg acaaagccag tgaaccgaac cgagctcaag gagagcttat | 960 |
| cgcacacgcg catgctgaaa agtcacgaga gtggcagcgc cgagaatgat ggctccggga | 1020 |
| acgatcccaa cgtcggaagc gccaagtctt cactcacaaa gctcaccaac ggggagaagg | 1080 |
| cagctggcgg ctcgggcgac ggcggttccg gtggtggtgg atctggacag ggacagaacg | 1140 |
| attccggaag cgataatgtt cgattgtata acgaaggtaa cgagaaatcg cgacgtcgcg | 1200 |
| aggctgaggc gatggatcga tgggccagtc gagagggcgg ttccggagac tgcggctctg | 1260 |
| gaggatccgg tcaaggcacc ggaagcggta gcggttcgca cgagggctcg ggttctggac | 1320 |
| agcgagattc gaacgaaaac gaaaagtttc gagggctgag cgtgcagctc atcaaggctc | 1380 |
| acggaggtgc gacgaccatg ctcgaactga gtttgcccga acactcgtcc gagcacgtcg | 1440 |
| tcgttcgacg atcgaactcg cgctccgcgt tcaagggatt ccaaacctac ctcaaaagtg | 1500 |
| agaagaagga aagttcagtg caaatgatga gcctagatct aacgcagcaa caacaccaat | 1560 |
| cgttttacga ggcatcctct atgatgccgc cggcggattt tgccagattt tacgggccca | 1620 |
| tcatgcctgc gggcatgccg ccgccgccaa tggatctacc cttaccgccg ccaccgtaca | 1680 |
| tcgacatgaa tcagtttacg gctgccgcgt tcacatcggc ctcgatccga cctgacatga | 1740 |
| tggattcgac cgcaaacccg ttctggagcg tgttgcaaac cgcggcggat cacacgcagc | 1800 |
| agacgagttc aagccaagcc gccgagcatc gcgccgcgcg gatccgacgc tttttgaaaa | 1860 |
| aacgcaagga gcgtaacttt gacaagaaag tccgttacgc ttcgaggcag cagctcgccg | 1920 |
| cgtctcgtcc tcgcttacgt ggacaatttg tacgcaacgc tgaggagacg acgactgaaa | 1980 |

```
acggctcaaa cggttctgac ggaaagaaat caaatgagtt caacgcgagc gccgccaaag    2040
gcgaagtcca gggcagagag gaacaatacg tcgatcgtca cggttccaac accggtacct    2100
cgaacgaggg ctcaaaggaa ggatcgcgaa gctcgtctcg cgacggctcc aagtga        2156

<210> SEQ ID NO 3
<211> LENGTH: 120
<212> TYPE: DNA
<213> ORGANISM: Ostreococcus tauri
<220> FEATURE:
<223> OTHER INFORMATION: HAPT promoter sequence

<400> SEQUENCE: 3
aaatactttt ccaggaaaag caggaaaaag gaatattctt taatattctc ggaatatttc     60
acgttcttgc ggcctggcga cgctgacggc gttacttcac gtcgcgcttt acccgtctcg    120

<210> SEQ ID NO 4
<211> LENGTH: 745
<212> TYPE: DNA
<213> ORGANISM: Ostreococcus tauri
<220> FEATURE:
<223> OTHER INFORMATION: Crd1 promoter sequence

<400> SEQUENCE: 4
tagatttccg atccgcgcgt tcgacgagcg cgcaaagagg gctcgcttcg agctcgcgat     60
cgagcgcgac gcgatgttcg ttcagtgaag ccacgcgatg agttagtcat cgcgttccaa    120
ggcacacgcg agcgcgcgtc gtccacgcga gcgagagcga gaactcgccg cccgtctcgt    180
cgactcaacc tagccaactt tgcagtgaaa gtaatcattc aaacgacgac cccacgcgcg    240
cgttcgcgtc caatctcacc acccgctcga acaccatcac caccgccctc gatctcacga    300
tccatcgtcc accgcgtccg cctccgtcgt caccgacctc cgcgtcgccc gcgcgtcgcg    360
tcgcgccgcg cccggaaacc attcccattg aacatcgctc gccccgcggg cgtctctcgg    420
gtgtgatcga ccactggcga tctcacacag acgtcacaca cccagaatac gtcacatcca    480
tcgataaaaa aatcaccccc cgtccgtccc gcggatcgcc tcgttcgcgt ccgtgacggc    540
cataaacacc accgcactac gagtgggcga aatcgcgaaa tcttatccgc ccccgtgatt    600
cgctcgcgtc cgtgtgtggg cacaccacga gtgatcactc gtggaagagt ccctctgcgg    660
acgtccggtg cgtcccgtga cgtcgcgcgc gcgtcgtccg cacttccccg cgcccgggac    720
gacgacgacg acgacgacga cgacc                                          745

<210> SEQ ID NO 5
<211> LENGTH: 443
<212> TYPE: DNA
<213> ORGANISM: Ostreococcus tauri
<220> FEATURE:
<223> OTHER INFORMATION: Cpx promoter sequence

<400> SEQUENCE: 5
cgacgcgtcg tgactccgcg ccacggggca tacgaacacc cggtcgtaga taccgcgccc     60
ccgccgggga cacggcgcga ctcacgacgc gtcgatgcga gacatctgtc caagagatcg    120
ggtgttggac gcaatcgcga tggcgcgcga tcgtcctgtg tgggcgaaca gtccgacggg    180
ggcgaccgat cgcacgacgc acgactcacg acgcgtcgat gcgagagaca tctgtccaag    240
agatcggtcc gacgggggcg accgatcgcc ccggcgcgc gatcgcgtcg ccgtcgacga    300
cgaccccgca cacgcgcgcg cgcgtcgacc gcgatatcgt gaacgaacga ggacgaattc    360
```

```
ttcgagcgat agcggggcgg gatgacgtcg aacgcgcgcg cgttcgacgc gcgagcgctc    420
gcgcgatgga cggttgcgga taa                                           443
```

<210> SEQ ID NO 6
<211> LENGTH: 810
<212> TYPE: DNA
<213> ORGANISM: Escherichia coli
<220> FEATURE:
<223> OTHER INFORMATION: KanMX (G418 resistance gene) sequence

<400> SEQUENCE: 6

```
atgggtaagg aaaagactca cgtttcgagg ccgcgattaa attccaacat ggatgctgat     60
ttatatgggt ataaatgggc tcgcgataat gtcgggcaat caggtgcgac aatctatcga    120
ttgtatggga agcccgatgc gccagagttg tttctgaaac atggcaaagg tagcgttgcc    180
aatgatgtta cagatgagat ggtcagacta aactggctga cggaatttat gcctcttccg    240
accatcaagc attttatccg tactcctgat gatgcatggt tactcaccac tgcgatcccc    300
ggcaaaacag cattccaggt attagaagaa tatcctgatt caggtgaaaa tattgttgat    360
gcgctggcag tgttcctgcg ccggttgcat tcgattcctg tttgtaattg tccttttaac    420
agcgatcgcg tatttcgtct cgctcaggcg caatcacgaa tgaataacgg tttggttgat    480
gcgagtgatt ttgatgacga gcgtaatggc tggcctgttg aacaagtctg gaaagaaatg    540
cataagcttt tgccattctc accggattca gtcgtcactc atggtgattt ctcacttgat    600
aaccttattt ttgacgaggg gaaattaata ggttgtattg atgttggacg agtcggaatc    660
gcagaccgat accaggatct tgccatccta tggaactgcc tcggtgagtt ttctccttca    720
ttacagaaac ggctttttca aaaatatggt attgataatc ctgatatgaa taaattgcag    780
tttcatttga tgctcgatga gttttctaa                                     810
```

<210> SEQ ID NO 7
<211> LENGTH: 265
<212> TYPE: DNA
<213> ORGANISM: Ashbya gossypii
<220> FEATURE:
<223> OTHER INFORMATION: TEF Terminator sequence

<400> SEQUENCE: 7

```
tcagtactga caataaaaag attcttgttt tcaagaactt gtcatttgta tagttttttt     60
atattgtagt tgttctattt taatcaaatg ttagcgtgat ttatattttt tttcgcctcg    120
acatcatctg cccagatgcg aagttaagtg cgcagaaagt aatatcatgc gtcaatcgta    180
tgtgaatgct ggtcgctata ctgctgtcga ttcgatacta acgccgccat ccagtgtcga    240
aaacgagctc tcgagaaccc ttaat                                         265
```

<210> SEQ ID NO 8
<211> LENGTH: 252
<212> TYPE: DNA
<213> ORGANISM: Agrobacterium tumefaciens
<220> FEATURE:
<223> OTHER INFORMATION: Nos terminator sequence

<400> SEQUENCE: 8

```
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggtttttatg attagagtcc cgcaattata catttaatac    180
```

| | |
|---|---|
| gcgatagaaa acaaaatata gcgcgcaaac taggataaat tatcgcgcgc ggtgtcatct | 240 |
| atgttactag at | 252 |

<210> SEQ ID NO 9
<211> LENGTH: 572
<212> TYPE: DNA
<213> ORGANISM: Streptomyces noursei
<220> FEATURE:
<223> OTHER INFORMATION: Nourseothricin acetyltransferase resistance gene Nat1

<400> SEQUENCE: 9

| | |
|---|---|
| atgaccactc ttgacgacac ggcttaccgg taccgcacca gtgtcccggg ggacgccgag | 60 |
| gccatcgagg cactggatgg gtccttcacc accgacaccg tcttccgcgt caccgccacc | 120 |
| ggggacggct tcaccctgcg ggaggtgccg gtggacccgc ccctgaccaa ggtgttcccc | 180 |
| gacgacgaat cggacgacga atcggacgac ggggaggacg cgacccggac ctcccggacg | 240 |
| ttcgtcgcgt acgggacgac ggcgacctg gcgggcttcg tggtcatctc gtactcggcg | 300 |
| tggaaccgcc ggctgaccgt cgaggacatc gaggtcgccc ggagcaccg ggggcacggg | 360 |
| gtcgggcgcg cgttgatggg gctcgcgacg gagttcgccg gcgagcgggg cgccgggcac | 420 |
| ctctggctgg aggtcaccaa cgtcaacgca ccggcgatcc acgcgtaccg gcggatgggg | 480 |
| ttcaccctct gcggcctgga caccgccctg tacgacggca ccgcctcgga cggcgagcgg | 540 |
| caggcgctct aatgagcatg ccctgcccct ag | 572 |

<210> SEQ ID NO 10
<211> LENGTH: 1653
<212> TYPE: DNA
<213> ORGANISM: Unknown
<220> FEATURE:
<223> OTHER INFORMATION: Description of Unknown: Firefly Luciferase sequence

<400> SEQUENCE: 10

| | |
|---|---|
| atggaagacg ccaaaaacat aaagaaaggc ccggcgccat tctatccgct ggaagatgga | 60 |
| accgctggag agcaactgca taaggctatg aagagatacg ccctggttcc tggaacaatt | 120 |
| gcttttacag atgcacatat cgaggtggac atcacttacg ctgagtactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgggcatt | 360 |
| tcgcagccta ccgtggtgtt cgtttccaaa aagggggttgc aaaaaatttt gaacgtgcaa | 420 |
| aaaaagctcc caatcatcca aaaaattatt atcatggatt ctaaaacgga ttaccaggga | 480 |
| tttcagtcga tgtacacgtt cgtcacatct catctacctc ccggttttaa tgaatacgat | 540 |
| tttgtgccag agtccttcga tagggacaag acaattgcac tgatcatgaa ctcctctgga | 600 |
| tctactggtc tgcctaaagg tgtcgctctg cctcatagaa ctgcctgcgt gagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttc tgaggagcct tcaggattac | 840 |
| aagattcaaa gtgcgctgct ggtgccaacc ctattctcct tcttcgccaa agcactctg | 900 |
| attgacaaat acgatttatc taatttacac gaaattgctt ctggtggcgc tcccctctct | 960 |
| aaggaagtcg gggaagcggt tgccaagagg ttccatctgc caggtatcag gcaaggatat | 1020 |

```
gggctcactg agactacatc agctattctg attacacccg aggggatga taaaccgggc    1080 gcggtcggta agttgttcc atttttgaa gcgaaggttg tggatctgga taccgggaaa    1140
acgctgggcg ttaatcaaag aggcgaactg tgtgtgagag gtcctatgat tatgtccggt    1200
tatgtaaaca atccggaagc gaccaacgcc ttgattgaca aggatggatg gctacattct    1260
ggagacatag cttactggga cgaagacgaa cacttcttca tcgttgaccg cctgaagtct    1320
ctgattaagt acaaaggcta tcaggtggct cccgctgaat tggaatccat cttgctccaa    1380
caccccaaca tcttcgacgc aggtgtcgca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aggtcttac cggaaaactc gacgcaagaa aaatcagaga gatcctcata    1620
aaggccaaga agggcggaaa gatcgccgtg taa    1653
```

<210> SEQ ID NO 11
<211> LENGTH: 3704
<212> TYPE: DNA
<213> ORGANISM: Artificial Sequence
<220> FEATURE:
<223> OTHER INFORMATION: Description of Artificial Sequence: Synthetic
      PAG25 yeast vector

<400> SEQUENCE: 11

```
gaacgcggcc gccagctgaa gcttcgtacg ctgcaggtcg acggatcccc gggttaatta     60
aggcgcgcca gatctgttta gcttgccttg tccccgccgg gtcacccggc cagcgacatg    120
gaggcccaga ataccctcct tgacagtctt gacgtgcgca gctcaggggc atgatgtgac    180
tgtcgcccgt acatttagcc catacatccc catgtataat catttgcatc catacatttt    240
gatggccgca cggcgcgaag caaaaattac ggctcctcgc tgcagacctg cgagcaggga    300
aacgctcccc tcacagacgc gttgaattgt ccccacgccg cgcccctgta gagaaatata    360
aaaggttagg atttgccact gaggttcttc tttcatatac ttccttttaa aatcttgcta    420
ggatacagtt ctcacatcac atccgaacat aaacaaccat gggtaccact cttgacgaca    480
cggcttaccg gtaccgcacc agtgtcccgg ggacgccga ggccatcgag gcactggatg    540
ggtccttcac caccgacacc gtcttccgcg tcaccgccac cggggacggc ttcaccctgc    600
gggaggtgcc ggtggacccg cccctgacca aggtgttccc cgacgacgaa tcggacgacg    660
aatcggacga cggggaggac ggcgaccegg actcccggac gttcgtcgcg tacggggacg    720
acggcgacct gcgggcttc gtggtcgtct cgtactccgg ctggaaccgc cggctgaccg    780
tcgaggacat cgaggtcgcc ccggagcacc ggggcacgg ggtcgggcgc gcgttgatgg    840
ggctcgcgac ggagttcgcc cgcgagcggg cgccgggca cctctggctg gaggtcacca    900
acgtcaacgc accggcgatc cacgcgtacc ggcggatggg gttcacccte tgcggcctgg    960 acaccgccct gtacgacggc accgcctcgg acggcgagca ggcgctctac atgagcatgc   1020
cctgccccta atcagtactg acaataaaaa gattcttgtt ttcaagaact tgtcatttgt   1080 atagttttt tatattgtag ttgttctatt ttaatcaaat gttagcgtga tttatatttt   1140
ttttcgcctc gacatcatct gcccagatgc gaagttaagt gcgcagaaag taatatcatg   1200
cgtcaatcgt atgtgaatgc tggtcgctat actgctgtcg attcgatact aacgccgcca   1260
tccagtgtcg aaaacgagct cgaattcatc gatgatatca gatccactag tggcctatgc   1320
ggccgcggat ctgccggtct ccctatagtg agtcgtatta atttcgataa gccaggttaa   1380
```

```
cctgcattaa tgaatcggcc aacgcgcggg gagaggcggt ttgcgtattg ggcgctcttc    1440
cgcttcctcg ctcactgact cgctgcgctc ggtcgttcgg ctgcggcgag cggtatcagc    1500
tcactcaaag gcggtaatac ggttatccac agaatcaggg gataacgcag gaaagaacat    1560
gtgagcaaaa ggccagcaaa aggccaggaa ccgtaaaaag gccgcgttgc tggcgttttt    1620
ccataggctc cgcccccctg acgagcatca aaaaatcga cgctcaagtc agaggtggcg    1680
aaacccgaca ggactataaa gataccaggc gtttccccct ggaagctccc tcgtgcgctc    1740
tcctgttccg accctgccgc ttaccggata cctgtccgcc tttctccctt cgggaagcgt    1800
ggcgctttct caatgctcac gctgtaggta tctcagttcg gtgtaggtcg ttcgctccaa    1860
gctgggctgt gtgcacgaac cccccgttca gcccgaccgc tgcgccttat ccggtaacta    1920
tcgtcttgag tccaacccgg taagacacga cttatcgcca ctggcagcag ccactggtaa    1980
caggattagc agagcgaggt atgtaggcgg tgctacagag ttcttgaagt ggtggcctaa    2040
ctacggctac actagaagga cagtatttgg tatctgcgct ctgctgaagc cagttacctt    2100
cggaaaaaga gttggtagct cttgatccgg caaacaaacc accgctggta gcggtggttt    2160
ttttgtttgc aagcagcaga ttacgcgcag aaaaaaagga tctcaagaag atcctttgat    2220
cttttctacg gggtctgacg ctcagtggaa cgaaaactca cgttaaggga ttttggtcat    2280
gagattatca aaaaggatct tcacctagat ccttttaaat taaaaatgaa gttttaaatc    2340
aatctaaagt atatatgagt aaacttggtc tgacagttac caatgcttaa tcagtgaggc    2400
acctatctca gcgatctgtc tatttcgttc atccatagtt gcctgactcc ccgtcgtgta    2460
gataactacg atacgggagg gcttaccatc tggccccagt gctgcaatga taccgcgaga    2520
cccacgctca ccggctccag atttatcagc aataaaccag ccagccggaa gggccgagcg    2580
cagaagtggt cctgcaactt tatccgcctc catccagtct attaattgtt gccgggaagc    2640
tagagtaagt agttcgccag ttaatagttt gcgcaacgtt gttgccattg ctacaggcat    2700
cgtggtgtca cgctcgtcgt ttggtatggc ttcattcagc tccggttccc aacgatcaag    2760
gcgagttaca tgatccccca tgttgtgcaa aaaagcggtt agctccttcg gtcctccgat    2820
cgttgtcaga agtaagttgg ccgcagtgtt atcactcatg gttatggcag cactgcataa    2880
ttctcttact gtcatgccat ccgtaagatg cttttctgtg actggtgagt actcaaccaa    2940
gtcattctga gaatagtgta tgcggcgacc gagttgctct tgcccggcgt caatacggga    3000
taataccgcg ccacatagca gaactttaaa agtgctcatc attggaaaac gttcttcggg    3060
gcgaaaactc tcaaggatct taccgctgtt gagatccagt tcgatgtaac ccactcgtgc    3120
acccaactga tcttcagcat cttttacttt caccagcgtt tctgggtgag caaaaacagg    3180
aaggcaaaat gccgcaaaaa agggaataag ggcgacacgg aaatgttgaa tactcatact    3240 cttcctttt caatattatt gaagcattta tcagggttat tgtctcatga gcggatacat    3300
atttgaatgt atttagaaaa ataaacaaat aggggttccg cgcacatttc cccgaaaagt    3360
gccacctgac gtctaagaaa ccattattat catgacatta acctataaaa ataggcgtat    3420
cacgaggccc tttcgtctcg cgcgtttcgg tgatgacggt gaaaacctct gacacatgca    3480
gctcccggag acggtcacag cttgtctgta agcggatgcc gggagcagac aagcccgtca    3540
gggcgcgtca gcgggtgttg gcgggtgtcg ggctggctt aactatgcgg catcagagca    3600
gattgtactg agagtgcacc atatggacat attgtcgtta gaacgcggct acaattaata    3660
cataacctta tgtatcatac acatacgatt taggtgacac tata                    3704
```

```
<210> SEQ ID NO 12
<211> LENGTH: 4009
<212> TYPE: DNA
<213> ORGANISM: Artificial Sequence
<220> FEATURE:
<223> OTHER INFORMATION: Description of Artificial Sequence: Synthetic
      PUG6 vector

<400> SEQUENCE: 12
gaacgcggcc gccagctgaa gcttcgtacg ctgcaggtcg acaaccctta ataaacttc      60
gtataatgta tgctatacga agttattagg tctagagatc tgtttagctt gcctcgtccc    120
cgccgggtca cccggccagc gacatggagg cccagaatac cctccttgac agtcttgacg    180
tgcgcagctc aggggcatga tgtgactgtc gcccgtacat ttagcccata catccccatg    240
tataatcatt tgcatccata cattttgatg gccgcacggc gcgaagcaaa aattacggct    300
cctcgctgca gacctgcgag cagggaaacg ctcccctcac agacgcgttg aattgtcccc    360
acgccgcgcc cctgtagaga aatataaaag gttaggattt gccactgagg ttcttctttc    420
atatacttcc ttttaaaatc ttgctaggat acagttctca catcacatcc gaacataaac    480
aaccatgggt aaggaaaaga ctcacgtttc gaggccgcga ttaaattcca acatggatgc    540
tgatttatat gggtataaat gggctcgcga taatgtcggg caatcaggtg cgacaatcta    600
tcgattgtat gggaagcccg atgcgccaga gttgtttctg aaacatggca aggtagcgt    660
tgccaatgat gttacagatg agatggtcag actaaactgg ctgacggaat ttatgcctct    720
tccgaccatc aagcatttta tccgtactcc tgatgatgca tggttactca ccactgcgat    780
ccccggcaaa acagcattcc aggtattaga agaatatcct gattcaggtg aaaatattgt    840
tgatgcgctg gcagtgttcc tgcgccggtt gcattcgatt cctgtttgta attgtccttt    900
taacagcgat cgcgtatttc gtctcgctca ggcgcaatca cgaatgaata acggtttggt    960
tgatgcgagt gattttgatg acgagcgtaa tggctggcct gttgaacaag tctggaaaga   1020
aatgcataag cttttgccat tctcaccgga ttcagtcgtc actcatggtg atttctcact   1080
tgataacctt attttttgacg aggggaaatt aataggttgt attgatgttg gacgagtcgg   1140
aatcgcagac cgataccagg atcttgccat cctatggaac tgcctcggtg agttttctcc   1200
ttcattacag aaacggcttt ttcaaaaata tggtattgat aatcctgata tgaataaatt   1260
gcagtttcat ttgatgctcg atgagttttt ctaatcagta ctgacaataa aaagattctt   1320
gttttcaaga acttgtcatt tgtatagttt tttatattg tagttgttct attttaatca   1380
aatgttagcg tgatttatat ttttttttcgc ctcgacatca tctgcccaga tgcgaagtta   1440
agtgcgcaga aagtaatatc atgcgtcaat cgtatgtgaa tgctggtcgc tatactgctg   1500
tcgattcgat actaacgccg ccatccagtg tcgaaaacga gctctcgaga acccttaata   1560
taacttcgta taatgtatgc tatacgaagt tattaggtga tatcagatcc actagtggcc   1620
tatgcggccg cggatctgcc ggtctcccta gtgagtcg tattaatttc gataagccag   1680
gttaacctgc attaatgaat cggccaacgc gcggggagag gcggtttgcg tattgggcgc   1740
tcttccgctt cctcgctcac tgactcgctg cgctcggtcg ttcggctgcg gcgagcggta   1800
tcagctcact caaaggcggt aatacggtta tccacagaat cagggaataa gcaggaaag   1860
aacatgtgag caaaaggcca gcaaaaggcc aggaaccgta aaaaggccgc gttgctggcg   1920
ttttttccata ggctccgccc ccctgacgag catcacaaaa atcgacgctc aagtcagagg   1980
tggcgaaacc cgacaggact ataaagatac caggcgtttc ccctggaag ctccctcgtg   2040
```

```
cgctctcctg ttccgaccct gccgcttacc ggatacctgt ccgcctttct cccttcggga    2100
agcgtggcgc tttctcaatg ctcacgctgt aggtatctca gttcggtgta ggtcgttcgc    2160
tccaagctgg gctgtgtgca cgaaccccc gttcagcccg accgctgcgc cttatccggt    2220
aactatcgtc ttgagtccaa cccggtaaga cacgacttat cgccactggc agcagccact    2280
ggtaacagga ttagcagagc gaggtatgta ggcggtgcta cagagttctt gaagtggtgg    2340
cctaactacg gctacactag aaggacagta tttggtatct gcgctctgct gaagccagtt    2400
accttcggaa aaagagttgg tagctcttga tccggcaaac aaaccaccgc tggtagcggt    2460
ggtttttttg tttgcaagca gcagattacg cgcagaaaaa aaggatctca agaagatcct    2520
ttgatctttt ctacggggtc tgacgctcag tggaacgaaa actcacgtta agggattttg    2580
gtcatgagat tatcaaaaag gatcttcacc tagatccttt aaattaaaaa tgaagtttt    2640 aaatcaatct aaagtatata tgagtaaact tggtctgaca gttaccaatg cttaatcagt    2700
gaggcaccta tctcagcgat ctgtctattt cgttcatcca tagttgcctg actccccgtc    2760
gtgtagataa ctacgatacg ggagggctta ccatctggcc ccagtgctgc aatgataccg    2820
cgagacccac gctcaccggc tccagattta tcagcaataa accagccagc cggaagggcc    2880
gagcgcagaa gtggtcctgc aactttatcc gcctccatcc agtctattaa ttgttgccgg    2940
gaagctagag taagtagttc gccagttaat agtttgcgca acgttgttgc cattgctaca    3000
ggcatcgtgg tgtcacgctc gtcgtttggt atggcttcat tcagctccgg ttcccaacga    3060
tcaaggcgag ttacatgatc ccccatgttg tgcaaaaaag cggttagctc cttcggtcct    3120
ccgatcgttg tcagaagtaa gttggccgca gtgttatcac tcatggttat ggcagcactg    3180
cataattctc ttactgtcat gccatccgta agatgctttt ctgtgactgg tgagtactca    3240
accaagtcat tctgagaata gtgtatgcgg cgaccgagtt gctcttgccc ggcgtcaata    3300
cgggataata ccgcgccaca tagcagaact ttaaaagtgc tcatcattgg aaaacgttct    3360
tcggggcgaa aactctcaag gatcttaccg ctgttgagat ccagttcgat gtaacccact    3420
cgtgcaccca actgatcttc agcatctttt actttcacca gcgtttctgg gtgagcaaaa    3480
acaggaaggc aaaatgccgc aaaaaaggga ataagggcga cacggaaatg ttgaatactc    3540
atactcttcc tttttcaata ttattgaagc atttatcagg gttattgtct catgagcgga    3600
tacatatttg aatgtattta gaaaaataaa caatagggg ttccgcgcac atttccccga    3660
aaagtgccac ctgacgtcta agaaaccatt attatcatga cattaaccta taaaaatagg    3720
cgtatcacga ggccctttcg tctcgcgcgt ttcggtgatg acggtgaaaa cctctgacac    3780
atgcagctcc cggagacggt cacagcttgt ctgtaagcgg atgccgggag cagacaagcc    3840
cgtcagggcg cgtcagcggg tgttggcggg tgtcggggct ggcttaacta tgcggcatca    3900
gagcagattg tactgagagt gcaccatatg gacatattgt cgttagaacg cggctacaat    3960
taatacataa ccttatgtat catacacata cgatttaggt gacactata                4009
```

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer ot-H4 For

<400> SEQUENCE: 13
gcggatccca cggagcgcaa cggtacc                                         27

```
<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer ot-H4 Rev

<400> SEQUENCE: 14
ccagcgccag ccatggtttt cgaacg                                           26

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer TOC1fullfuRNco1

<400> SEQUENCE: 15
tttccatgga cttggagccg tcgcgaga                                         28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer TOC1fullFNhe1

<400> SEQUENCE: 16
tttgctagca cctcgagccg ggaccaaaaa                                       30

<210> SEQ ID NO 17
<211> LENGTH: 62
<212> TYPE: DNA
<213> ORGANISM: Artificial Sequence
<220> FEATURE:
<223> OTHER INFORMATION: Description of Artificial Sequence: Synthetic
      sequence encoding a 6Xhistidine tag

<400> SEQUENCE: 17 cgggcccttta cgtacctagg aagcttctcg agcaccacca ccaccaccac tgactcgagt     60
ga                                                                    62

<210> SEQ ID NO 18
<211> LENGTH: 62
<212> TYPE: DNA
<213> ORGANISM: Artificial Sequence
<220> FEATURE:
<223> OTHER INFORMATION: Description of Artificial Sequence: Synthetic
      complementary sequence encoding 6Xhistidine tag

<400> SEQUENCE: 18
gcccgccaat gcatggatcc ttcgaagagc tcgtggtggt ggtggtggtg actgagctca     60
ct                                                                    62
```